United States Patent [19]

Peterson

[11] Patent Number: 4,469,635

[45] Date of Patent: Sep. 4, 1984

[54] POLYOL ESTERS OF ALPHA-HYDROXY CARBOXYLIC ACIDS

[75] Inventor: Donald J. Peterson, Cincinnati, Ohio

[73] Assignee: The Procter & Gamble Company, Cincinnati, Ohio

[21] Appl. No.: 370,775

[22] Filed: Apr. 22, 1982

Related U.S. Application Data

[60] Division of Ser. No. 219,718, Dec. 24, 1980, , which is a continuation-in-part of Ser. No. 124,192, Feb. 25, 1980.

[51] Int. Cl.$^3$ .......................... C07F 9/02; C07F 9/10; C11C 3/00; A23J 7/00
[52] U.S. Cl. ...................................................... 260/403
[58] Field of Search ......................................... 260/403

[56] References Cited

U.S. PATENT DOCUMENTS

| | | | |
|---|---|---|---|
| 2,573,650 | 10/1951 | Peterson et al. | 252/28 |
| 2,652,410 | 9/1953 | Cunningham et al. | 260/404.5 |
| 2,690,971 | 10/1954 | Iveson et al. | 99/118 |
| 2,694,474 | 9/1972 | Eibl et al. | 260/403 |
| 2,721,188 | 10/1955 | Polly et al. | 260/410.6 X |
| 2,957,932 | 10/1960 | Radlove et al. | 260/410.8 |
| 2,966,410 | 12/1960 | Chang et al. | 99/118 |
| 3,275,667 | 9/1966 | Bohunek | 260/403 |
| 3,347,848 | 10/1967 | Ismail et al. | 536/119 |
| 3,622,605 | 11/1971 | DeJong et al. | 260/410.6 |
| 3,681,412 | 8/1972 | Betzing | 260/403 |
| 3,704,254 | 11/1972 | Aneja | 260/403 |
| 3,960,905 | 6/1976 | Eibl et al. | 260/403 |
| 4,130,571 | 12/1978 | Nakajima et al. | 260/403 |
| 4,160,773 | 7/1979 | Eibl et al. | 260/403 |
| 4,320,121 | 3/1982 | Sears | 260/403 |

FOREIGN PATENT DOCUMENTS 49-55752  5/1974  Japan .
180181  3/1966  U.S.S.R. .

OTHER PUBLICATIONS

Simonis, et al., Detergent Activity of Hydroxylated Esters of Saccharose and Fatty Acids, Angew. Chem., 75(16/17):791, (1963).
Tulloch, et al., Extracellular Glycolipids of Rhodotorula Species, Canadian Journal of Chemistry, 42:830–835, (1964).

Primary Examiner—Helen M. S. Sneed
Attorney, Agent, or Firm—Jacobus C. Rasser; Donald E. Hasse; Steven J. Goldstein

[57] ABSTRACT

Polyol esters of alpha-hydroxy carboxylic acids are disclosed which are excellent oil-in-water emulsifiers for food products, drug delivery vehicles, cosmetic ointments and the like. The compounds are also useful as detergent surfactants and can be combined with co-surfactants, builders and detergent adjunct materials.

4 Claims, No Drawings

POLYOL ESTERS OF ALPHA-HYDROXY CARBOXYLIC ACIDS

This is a division of application Ser. No. 219,718 filed Dec. 24, 1980 which is a continuation-in-part of Ser. No. 124,192 filed Feb. 25, 1980.

TECHNICAL FIELD

The present invention relates to compounds which are polyol esters of alpha-hydroxy carboxylic acids. The compounds herein are all monoesters of the alpha-hydroxy acids, except where the polyol is a glycerol phosphoric acid ester (e.g., glycerol phosphatidyl choline ester), in which case the compounds contain 1 or 2 alpha-hydroxy acid chains.

The alpha-hydroxy acid polyol esters herein exhibit superior emulsifying properties, as compared with their non-hydroxylated counterparts known in the art, and are particularly useful as oil-in-water emulsifying agents for food products, drug delivery vehicles, cosmetic ointments, and the like. The superiority of the present emulsifiers is demonstrated by the fact that they provide oil-in-water emulsions having extremely fine oil droplet sizes and high stability toward oil droplet coalescense and phase separation. Moreover, such emulsions can be prepared over a wider temperature range that that possible with the corresponding non-hydroxylated emulsifiers. The above benefits are especially useful in the manufacture of ingestible emulsions formulated with substantial amounts of fats or oils, such as salad dressings, peanut butter, candy, and icing. The compounds herein also exhibit antimicrobial properties which contribute to the storage-stability of emulsions containing them.

The alpha-hydroxy acid polyol esters of the present invention are also useful as detergent surfactants which can be used as total or partial replacements for nonionic surfactants commonly used in the detergent industry. Conventional nonionic surfactants are generally derived from petrochemicals and are especially effective at removing greasy or oily soils from fabrics. The present compounds are also highly effective at removing oily soils from fabrics. Additionally, they can be manufactured from renewable resources, i.e., animal and vegetable fats and oils, which makes them potentially more cost effective than the petroleum-based surfactants. Finally, the compounds herein provide excellent cleaning in cool or cold water (e.g., 5°–20° C.) fabric laundering operations. Besides the obvious economical benefits, there are many convenience and fabric care benefits to be obtained from cold water laundering. For example, dye transfer between fabrics is diminished, thereby making it possible to launder mixed colored fabrics without sorting them. Laundering in cold water also results in less wrinkling of fabrics, and avoids damage (e.g., shrinkage) to delicate fabrics which should not be washed in hot water.

BACKGROUND ART

Various long-chain fatty acid glycerides containing short-chain hydroxy acid substituents have been disclosed in the art for use primarily as food emulsifiers. For example, U.S. Pat. No. 2,690,971, Iveson, et al., issued Oct. 5, 1954, relates to shortening addition agents formed by reacting glycerine, higher fatty acids containing from 12 to 20 carbon atoms, and alpha-hydroxy acids containing less than 6 carbon atoms. Mixed diglycerides containing both the long-chain acid and short-chain hydroxy acid groups are the desired product, but up to 25% monoglycerides, including short-chain alpha-hydroxy monoglycerides, are formed in the reaction. Similar short-chain alpha-hydroxy monoglycerides are disclosed in U.S. Pat. No. 2,957,932, Radlove, et al., issued Oct. 25, 1960 and in U.S. Pat. No. 2,966,410 Chang, et al., issued Dec. 27, 1960.

Long-chain alpha-hydroxy monoglyceride compounds have also been disclosed in the art. For example, Japanese Pat. No. 49-55752, Uoi, et al., published May 30, 1974, discloses polycarbonate-resin molding compositions containing minor amounts of higher alpha-hydroxy fatty acid monoglycerides as mold-release and fluidizing agents. The patent states that its alpha-hydroxy acids should have long hydrocarbon chains and exhibit relatively high melting points. Only alpha-hydroxy palmitic, stearic and arachidonic acid monoglycerides are disclosed. Also, U.S. Pat. No. 2,108,725, Rieche, et al., issued Feb. 15, 1938, describes compounds of the formula $RCH(X)COR^1$ where X is a hydrophilic radical which can be hydroxy, amino or ammonio and $R^1$ is hydroxy, an alcohol radical or a substituted or unsubstituted amine. The compounds are derived from alpha-halo fatty acids and are said to be useful as emulsifying, cleaning or softening agents. Example VI describes the preparation of alpha-hydroxy stearic acid from alpha-bromo stearic acid. In the form of its monoglyceride, the product is said to be a highly active emulsifying agent for the preparation of pastes, ointments, and creams, especially for cosmetics.

Various sugar esters of hydroxy fatty acids are described in the art. For example, Simonis, et al., Detergent Activity of Hydroxylated Esters of Saccharose and Fatty Acids, Agnew. Chem., 75(16/17): 791 (1963), discloses that esters of sugars and fatty acids containing 1 or more hydroxy groups possess high detergent activity. Examples include saccharose 12-hydroxystearate and saccharose 9,10-dihydroxystearate. Also, Tulloch, et al., Extracellular Glycolipids of Rhodotorula Species, Canadian Journal of Chemistry, 42:830–835 (1964), discloses the biosynthesis of extracellular glycolipids from several species of red yeast. The glycolipids consist of a mixture of the mannitol and pentitol esters of beta-hydroxy palmitic and stearic acids.

Finally, U.S. Pat. No. 2,652,410, Cunningham, et al., issued Sept. 15, 1953, discloses the reaction of alpha-hydroxy acids and/or their estolides with polyhydric alcohols to form partly or completely gelled esterification mixtures. The gelled mixtures are said to be useful as linoleum cementing compositions, and when highly dehydroxylated, as substitutes for linseed oil and drying oils. The patent states that four possible reactions may occur singly, simultaneously or consecutively, depending on the reaction conditions. They are estolide formation, esterification of the acids and estolides, dehydroxylation of the acids, estolides and esters, and polymerization.

SUMMARY OF THE INVENTION

The present invention encompasses compounds which are polyol monoesters of an alpha-hydroxy carboxylic acid of the formula $$\text{RCHCOH,} \atop \underset{\text{OH}}{|}\ \overset{\overset{\text{O}}{\|}}{}$$

wherein R is a hydrocarbyl group containing from about 6 to about 20 carbon atoms and the polyol is selected from the group consisting of:
  (a) glycols containing from 1 to about 20 $C_2$–$C_3$ alkylene oxide units and mixtures thereof;
  (b) glycerols of the formula $$\text{HO(CH}_2\overset{\overset{\text{OH}}{|}}{\text{CH}}\text{CH}_2\text{O)}_n\text{H,}$$

wherein n is from 1 to 10, and isomers thereof, provided that R is a hydrocarbyl group containing from about 6 to about 12 carbon atoms when n is 1;
  (c) polyols of the formula $$\text{HOCH}_2(\overset{\overset{\text{OH}}{|}}{\text{CH}})_n\text{CH}_2\text{OH,}$$

wherein n is from 2 to 4;
  (d) pentaerythritol and dipentaerythritol;
  (e) inositol; and
  (f) monosaccharides and disaccharides containing 5 or 6 carbon atoms per saccharide unit.

The invention also encompasses compounds which are polyol monoesters or diesters of an alpha-hydroxy carboxylic acid of the formula $$\text{RCHCOH,} \atop \underset{\text{OH}}{|}\ \overset{\overset{\text{O}}{\|}}{}$$

wherein R is a hydrocarbyl group containing from about 6 to about 20 carbon atoms and the polyol is the choline or ethanolamine ester of glycerol phosphoric acid having 0 or 1 of its hydroxyl groups esterified with a carboxylic acid containing from about 8 to about 22 carbon atoms.

Emulsions and detergent compositions comprising the above alpha-hydroxy acid polyol esters are also part of the present invention.

DETAILED DESCRIPTION OF THE INVENTION

The alpha-hydroxy acid polyol esters herein are especially useful as emulsifiers which provide oil-in-water emulsions of high stability toward oil droplet coalescence and eventual phase separation. This improved stability is, at least in part, attributable to the extremely fine oil droplet size obtained using the present emulsifiers. The stable emulsions or emulsifiable mixtures herein can also be prepared over a wider temperature range than that possible using conventional emulsifier compounds.

Oil-in-water emulsifiers function by forming a thin emulsifier film around oil droplets dispersed throughout the water-continuous phase. A hydration layer forms around the emulsifier film and acts as an additional barrier to oil droplet flocculation and coalescence. While not intending to be limited by theory, it is believed that the present compounds are improved oil-in-water emulsifiers because the hydroxyl group at the alpha-carbon atom of the carboxylic acid moiety provides an additional point of hydration and increases the width of the hydration layer formed around the emulsifier film. Thus, the present emulsifiers provide emulsions having greater stability toward oil droplet flocculation and coalescence, and eventual phase separation.

The alpha-hydroxy polyol esters herein are also useful as detergent surfactants which are highly effective at removing greasy/oily type soils from fabrics. It is believed that they readily adsorb at oil/water interfaces where they reduce interfacial tension and cause the soil to roll up, so that it can be more easily removed by mechanical action. The present compounds then effectively emulsify the oily soil and prevent its redeposition on fabrics.

The alpha-hydroxy acid polyol esters herein are prepared by reacting an alpha-hydroxy carboxylic acid of the formula RCH(OH)COOH with the appropriate polyol. The R substituent of the alpha-hydroxy carboxylic acid can be any hydrocarbyl group containing from about 6 to about 20 carbon atoms. For example, R can be straight- or branched-chain alkyl, alkenyl, alkynyl, alkaryl (e.g., alkylphenyl or alkylbenzyl), substituted hydrocarbyl, and the like. The nature of substituent R can be varied by proper selection of the carboxylic acid used in the reaction scheme, as disclosed hereinafter. Preferably, R is an alkyl group having from about 8 to about 18 carbon atoms, more preferably from about 10 to about 16 carbon atoms.

The polyol portion of the alpha-hydroxy acid polyol monoester compounds herein can be any glycol containing from 1 to about 20 $C_2$–$C_3$ alkylene oxide units and mixtures thereof. Examples include ethylene glycol, propylene glycol, 1,3-propylene glycol, and glycols containing up to about 20 ethylene oxide, propylene oxide, or mixed ethylene oxide/propylene oxide units. Mixed ethylene oxide/propylene oxide glycols useful herein include the class of materials sold by BASF Wyandotte under the tradename PLURONIC, which are copolymers of polyoxypropylene and polyoxyethylene glycols in which the polyoxyethylene groups are added to both sides of a polyoxypropylene chain. Preferred glycols are those containing from 1 to about 10 ethylene oxide or propylene oxide units. Propylene glycol is especially preferred.

The polyol portion of the polyol monoesters herein can also be a glycerol of the formula $$\text{HO(CH}_2\overset{\overset{\text{OH}}{|}}{\text{CH}}\text{CH}_2\text{O)}_n\text{H,}$$

wherein n is from 1 to 10, and isomers thereof. Preferred compounds of this class are those wherein n is from 1 to 5 and most preferably, is glycerol (i.e., n equals 1). Polyglycerols (i.e., n is from 2 to 10) are well-known polymers formed by the dehydration of glycerol. For each unit of glycerol added to the polymer chain, there is an increase of one hydroxyl group. Useful polyglycerols also include the isomers of those described by the above general formula. Such isomers can be formed by polymerization from a secondary hydroxyl group of the parent glycerol, rather than from a primary hydroxyl group. For example, the compound

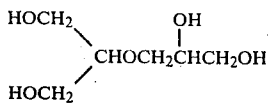

is an isomer of

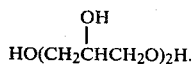

The higher polyols of the formula

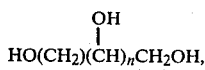

wherein n is from 2 to 4, are also useful as the polyol component herein. Examples include erythritol, xylitol, sorbitol, mannitol, glucitol, talitol, lyxitol, galactitol, rhamnitol, iditol, dulcitol, and allitol. Preferred polyols of this class are erythritol, xylitol and sorbitol.

Other suitable polyols for forming the polyol monoesters herein include pentaerythritol, dipentaerythritol, and inositol.

The monosaccharides and disaccharides containing 5 or 6 carbon atoms per saccharide unit are also useful as the polyol portion of the polyol monoesters herein. Monosaccharides having 5 carbon atoms include ribose, arabinose, cyclose, xylose, and lyxose. Monosaccharides having 6 carbon atoms include allose, altrose, glucose, mannose, gulose, idose, galactose, talose, fructose, and sorbose. Suitable disaccharides include maltose, cellobiose, sucrose, and lactose. Preferred polyols of this class are glucose, fructose, and sucrose, and especially sucrose.

An especially preferred group of polyol monoesters herein because of their excellent emulsifying and detergency properties are those in which substituent R of the alpha-hydroxy carboxylic acid is an alkyl group containing from about 10 to about 16 carbon atoms and the polyol is propylene glycol, glycerol or sucrose.

The present invention also includes compounds which are polyol monoesters or diesters of alpha-hydroxy carboxylic acids, wherein the polyol is the choline or ethanolamine ester of glycerol phosphoric acid having 0 or 1 of its hydroxyl groups esterified with a carboxylic acid containing from about 8 to about 22 carbon atoms. Such compounds can contain 1 alpha-hydroxy carboxylic acid group (i.e., are polyol monoesters of the alpha-hydroxy acids), in which case the other hydroxyl group can be, but need not be, esterified with a C$_8$–C$_{22}$ carboxylic acid group. However, it is preferred, for ease of synthesis, that they contain 2 alpha-hydroxy carboxylic acid groups (i.e., are polyol diesters of the alpha-hydroxy acids). Thus, the compounds of this class are alpha-hydroxy carboxylic acid derivatives of the well-known lecithin and cephalin compounds, and their lyso analogs. Examples include 1,3- and 1,2-di(alpha-hydroxy stearic acid) phosphatidyl choline; 1-(alpha-hydroxy lauric acid), 2-(lauric acid) phosphatidyl choline; 1-(alpha-hydroxy palmitic acid) phosphatidyl choline; 1,2-di(alpha-hydroxy tallow fatty acid) phosphatidyl ethanolamine; and 2-(alpha-hydroxy stearic acid) phosphatidyl ethanolamine.

The economical practice of the present invention on an industrial scale ultimately depends on a ready source of alpha-hydroxy carboxylic acids. Alpha-hydroxy acids can be prepared from alpha-bromo acids, which in turn are available via the Hell-Volhard-Zelinsky reaction. However, H-V-Z alpha-bromo acids are quite expensive. Fortunately, high quality, low cost alpha-chloro acids suitable for use in preparing the compounds of the present invention are available via the process disclosed in U.S. Pat. No. 4,148,811, Crawford, issued Apr. 10, 1979, incorporated herein by reference, using tetracyanoquinodimethane (TCNQ) as the catalyst. Additionally, a preferred process for preparing a precursor of TCNQ, 1,4-bis(dicyanomethylene) cyclohexane, is disclosed in U.S. Pat. No. 4,229,364, Crawford, issued Oct. 21, 1980, incorporated herein by reference.

The preferred overall reaction scheme for preparing the alpha-hydroxy acid polyol esters herein is illustrated as follows, using glycerol as the polyol.

Step 1-Preparation of alpha-chloro acid

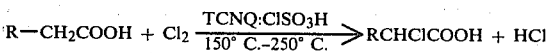

Step 2-Preparation of alpha-hydroxy acid and 2-methoxyester

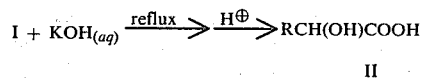

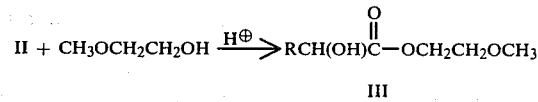

Step 3 Preparation of alpha-hydroxy monoglyceride

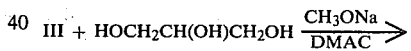

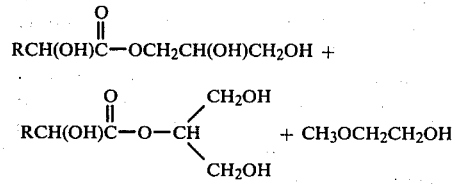

The following is a typical and preferred synthesis of alpha-hydroxy monolaurin following the foregoing scheme.

Preparation of Alpha-Hydroxy Monolaurin

Step 1. Alpha-chlorolauric acid was prepared by following the procedure of Example I of U.S. Pat. No. 4,148,811, Crawford.

Step 2. 0.1 Mole of alpha-chlorolauric acid prepared in the foregoing manner was admixed with 500 mls. water and 0.4 moles of KOH in a suitable reaction vessel and stirred overnight at a temperature of 98°–100° C. The reaction mixture was poured into a separatory funnel, to which was added hydrochloric acid (40 ml. conc. HCl in 200 ml. H$_2$O). The mixture was extracted with chloroform. The chloroform layer was removed and the CHCl$_3$ evaporated to yield alpha-hydroxylauric acid.

The alpha-hydroxylauric acid prepared in the foregoing manner was converted to the 2-methoxyethyl ester by refluxing a 5:1 molar ratio of 2-methoxyethanol with the acid in toluene solvent in the presence of a catalytic amount (0.3%) of p-toluenesulfonic acid. The reaction vessel was fitted with a moisture trap to remove $H_2O$ as it forms during the esterification. After water evolution was complete, the reaction mixture was water-washed and refined with 5% KOH/70:30 water:alcohol. The product was water-washed a second time, and the solvent was evaporated to yield 2-methoxyethyl alpha-hydroxylaurate.

Step 3. 12.6 Grams (0.046 moles) of 2-methoxyethyl alpha-hydroxylaurate, 40 g. glycerol (0.43 moles) and 0.2 g. sodium methoxide were dissolved in 200 mls. dimethyl acetamide (DMAC). The mixture was heated to 120° C. and stirred under vacuum (20 mm. Hg) to distill the DMAC and 2-methoxyethanol formed during the reaction. The residue was dissolved in chloroform and washed with 0.1% aqueous HCl and, thereafter, twice with fresh portions of water. The chloroform phase was dried with sodium sulfate, filtered and the chloroform removed under vacuum. The residue was dissolved in 10 volumes of hexane and cooled to 0° F. The hexane-soluble material was decanted from the insoluble oil layer and discarded. The oily layer was redissolved in hexane and the treatment repeated. The oily layer was vacuum dried and recovered to yield 12 g. (0.041 moles) (89% yield) of the titled compound, which was a mixture of the 1- and 2-positional isomers of alpha-hydroxy monolaurin. About 80% of the mixture was alpha-hydroxy monolaurin and about 20% was alpha-hydroxy-2-monolaurin. (Following common nomenclature, the 1-isomer carries no numerical designation and the 2-isomer is designated "2".)

Alpha-hydroxy monoglycerides of the present invention can be prepared using a variety of synthetic methods, although the reaction using the alpha-chloro acids in the manner disclosed above is preferred by virtue of the economical availability of the alpha-chloro acid via the process disclosed in U.S. Pat. No. 4,148,811, Crawford. Alternatively, alpha-bromo acids can be reacted with inorganic base to provide the alpha-hydroxy carboxylic acids used in the synthesis.

Step 2 of the synthesis is carried out using standard chemical techniques. For example, the KOH base can be replaced by sodium hydroxide, or with commercial, aqueous lye. Step 2 is conveniently carried out at from about 90° C. to 150° C.

In Step 3, methyl or other short-chain esters can be used in place of the 2-methoxyethyl ester disclosed. The DMAC solvent is not critical to the practice of Step 3, and, indeed, no solvent need be employed. The catalyst used in Step 3 can be any of the familiar glycerolysis catalysts, including various metal salts such as sodium hydride, various alkoxides such as sodium and potassium ethoxides, sodium glyceride, and the like. Step 3 is conveniently carried out at from about 90° C. to 150° C.

As noted above, the reaction provides mixtures of the 1- and 2-positional isomers of the alpha-hydroxy monoglycerides. Thermodynamically, the 1-isomers predominate and usually represent about 80-90% by weight of the product. The 1- and 2-isomers can be separated and the product purified by crystallization, chromatography, or molecular distillation, using procedures well-known in the art of fats and oils chemistry. However, it is to be understood that the mixed isomer reaction products are entirely satisfactory for use in the compositions of the present invention, and separation of the isomers into their pure components is entirely optional with the user. However, it is believed that the 1-isomers provide slightly better emulsions and may be preferred for this reason.

Preparation of Propylene Glycol Monoester of Alpha-Hydroxy Stearic Acid 15 g (0.048 moles) alpha-hydroxy methyl stearate, 38 g (0.5 moles) 1,2-propanediol and 0.2 g sodium methoxide were reacted in 100 ml DMAC. The solution was heated and stirred at 120° C. under partial vacuum (2 mm. Hg) to distill the DMAC and methanol formed during the reaction. The residue was dissolved in chloroform and washed successively with 0.1% aqueous HCl, 0.5% potassium carbonate in 50% aqueous ethanol, and twice with 50% aqueous ethanol. The chloroform phase was recovered and vacuum dried. The reaction product was purified in portions by florisil column chromatography. The sample was eluted with 1:1 ethyl ether:hexane. Fractions were collected and monitored by thin layer chromatography. Appropriate fractions were combined and dried under vacuum to yield 12 g (0.033 moles) (69% yield) of the titled compound.

Preparation of Sucrose Monoester of Alpha-Hydroxy Stearic Acid 15 g (0.048 moles) alpha-hydroxy methyl stearate, 140 g (0.41 moles) sucrose and 650 ml DMAC were heated and stirred at 110° C. to dissolve the components. 0.2 g sodium methoxide was added and the pressure reduced to distill about 300 ml of the DMAC at 120° C. The remaining solution was cooled and diluted with 1 liter of 0.3% aqueous acetic acid. The aqueous phase was extracted twice with 4:1 ethyl acetate:N-butanol (500 ml and 100 ml portions). The combined extracts were back-washed with water twice and the ethyl acetate phase dried under vacuum. The residue was crystallized twice from ethyl acetate at 0° F. The insoluble material was recovered and dried to yield 13 g (0.02 moles) (42% yield) of the titled compound.

As has been described above, the alpha-hydroxy acid polyol esters herein are especially useful as oil-in-water emulsifying agents for food products, drug delivery vehicles, cosmetic ointments, and the like. Thus, the compositions of the present invention are in the form of an emulsion or emulsifiable mixture, comprising:
  (a) an aqueous component,
  (b) a fat or oil component, the weight ratio of the fat or oil component to the aqueous component being from about 1:200 to about 5:1, and
  (c) from about 0.001% to about 10% by weight of the fat or oil component of the alpha-hydroxy acid polyol esters herein.

Typical cosmetic emulsions herein include those described in U.S. Pat. No. 4,017,641, Digiulio issued Apr. 12, 1977, incorporated herein by reference, and may be in the form of creams, lotions, oils, gels, jellies, lipsticks, foams and sprays. Suitable fat or oil components herein include the oils, waxes, and mixtures thereof described in the above patent in column 1, from lines 42 through 54. Examples are the lanolin fatty acids and isopropyl esters thereof, hydroxylated lanolin, the $C_{10}-C_{20}$ fatty acids and alcohols, and mixtures thereof. Typical optional components in such cosmetic emulsions include any of those described in column 3, from lines 32 to 50.

Typical ingestible compositions herein, including food products and drug delivery vehicles, are those wherein the fat or oil component of the composition is an edible, digestible glyceride. For example, lard, tallow, peanut oil, corn oil, sunflower seed oil, safflower oil, soybean oil, and the hydrogenation products thereof are preferred edible, digestible glycerides.

Low calorie ingestible compositions of the present invention employ, as the fat or oil component, edible, non-absorbable, non-digestible polyol fatty acid polyesters having at least 4 fatty acid ester groups, wherein each fatty acid group has from about 8 to about 22 carbon atoms. These polyol fatty acid polyesters, and their use in low calorie compositions, and fully disclosed in U.S. Pat. No. 3,600,186, Mattson, et al., issued Aug. 17, 1971; No. 3,954,976, Mattson, et al., issued May 4, 1976; No. 4,005,195, Jandacek, issued Jan. 25, 1977; No. 4,005,196, Jandacek, et al., issued Jan. 25, 1977; and No. 4,034,083, Mattson, issued July 5, 1977; all incorporated herein by reference.

As disclosed in the above patents, low calorie polyol polyesters include polyols having at least four hydroxyl groups (preferably, sucrose) esterified with a fatty acid having from about eight to about 22 carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be saturated or unsaturated, including positional and geometrical isomers, depending on the desired physical properties, for example liquid or solid, of the polyol fatty acid ester compound.

The following are examples of typical low calorie polyol fatty acid esters containing at least four fatty acid ester groups suitable for use in the present invention: glucose tetraoleate; glucose tetrastearate; glucose tetraester of mixed soybean oil fatty acids; mannose tetraester of tallow fatty acids; galactose tetraester of olive oil fatty acid; arabinose tetraester of cottonseed oil fatty acid; xylose tetralinoleate; galactose pentastearate; sucrose hexaoleate; sucrose octaoleate (preferred in low calorie oil products); sucrose octaester of substantially completely hydrogenated soybean oil fatty acid; sucrose octaester of peanut oil fatty acid.

The polyol fatty acid esters can be prepared by a variety of methods well known to those skilled in the art. These methods include: transesterification of the polyol with methyl, ethyl or glycerol fatty acid esters, acylation with a fatty acid chloride, acylation with a fatty acid anhydride and acylation with a fatty acid per se. As an example, the preparation of polyol fatty acid esters is described in U.S. Pat. No. 2,831,854, Tucker, et al., issued Apr. 22, 1958, incorporated herein by reference.

A method for preparing polyol fatty acid polyesters which is especially preferred for food compositions because it is solvent-free, does not generate difficult-to-remove contaminants, and produces high yields, is described in U.S. Pat. No. 3,963,699, Rizzi, et al., issued June 15, 1976, incorporated herein by reference.

As disclosed in U.S. Pat. Nos. 4,005,195 and 4,005,196, cited above, some of the liquid polyol polyesters undesirably pass through the anal sphincter. By combining the liquid polyester compositions with an anti-anal leakage agent ("AAL"), this undesired anal leakage effect is prevented.

One preferred class of materials which provide the anti-anal leakage effect herein includes fatty acids having a melting point of ca. 37° C. or higher, and ingestible, digestible sources of such fatty acids. The fatty acid AAL agents include, for example, the $C_{12}$–$C_{24}$ saturated fatty acids, and ingestible, digestible sources thereof. Highly preferred herein for their anti-anal leakage effect are the $C_{16}$–$C_{22}$, most preferably $C_{16}$–$C_{18}$, saturated fatty acids, or edible sources thereof. Hardened palm oil is an especially preferred AAL agent.

As is also disclosed in U.S. Pat. Nos. 4,005,195 and 4,005,196, the low calorie polyol polyesters can undesirably interfere with the uptake of fat soluble vitamins by the body, and could cause vitamin depletion. To avoid the vitamin depletion problem, the polyol polyesters can be fortified with fat-soluble vitamins, especially vitamin A, vitamin E, vitamin D, vitamin K, and mixtures thereof.

Advantageously, however, the above polyol polyesters also deplete the body's stores of cholesterol, thereby providing an antihypercholesterolemic benefit to the user.

Preferred polyol fatty acid polyesters for use herein are those wherein the polyol is erythritol, xylitol, sorbitol, glucose or sucrose (preferred). Especially preferred compounds of this type include the hexaoleate, heptaoleate and octaoleate of sucrose, and mixtures thereof.

The present invention provides a variety of useful food compositions. For example, a liquid salad dressing composition according to this invention contains one of the above-described alpha-hydroxy acid polyol ester emulsifiers, and has as its oil phase a liquid, digestible vegetable oil, and an aqueous phase comprising vinegar. A low calorie liquid salad dressing composition has as its oil phase a liquid, non-absorbable non-digestible polyol fatty acid polyester having at least 4 fatty acid ester groups, wherein each fatty acid group has from about 8 to about 22 carbon atoms, and an aqueous phase comprising vinegar.

A salad "cream" composition contains the emulsifier; an oil phase which is a digestible vegetable oil and represents at least about 70% by weight of the composition; and an aqueous phase comprising vinegar, natural or synthetic citrus juice, or mixtures thereof. A low calorie cream salad dressing uses as the oil phase the non-absorbable, non-digestible polyol fatty acid polyesters disclosed above. Such salad "creams" can be whipped to form a mayonnaise-type dressing or spread.

A nutritious beverage composition contains the emulsifier, water, an oil phase which is a digestible vegetable oil, and vegetable protein, or hydrolysate thereof, dissolved or suspended in the composition to provide nutritional benefits. Again, a low calorie nutritious beverage composition is made in like fashion using a non-absorbable, non-digestible polyol fatty acid polyester as the oil phase.

A dessert composition, ice cream, or the like, comprises the emulsifier, an oil phase which is a digestible vegetable oil, water, and milk solids dissolved or suspended therein. A low calorie version uses, as the oil phase; the non-absorbable non-digestible polyol fatty acid polyester.

An icing composition for cakes, cookies, and the like, employs the emulsifier, a digestible vegetable shortening as the "fat" phase and sugar plus water as the aqueous phase. As before, a low-calorie version of the icing uses the non-absorbable, non-digestible polyol fatty acid polyester.

A bread spread, or the like, composition akin to margarine has a digestible vegetable oil as its oil phase, water or milk as its aqueous phase, and a butter-like flavor component comprising diacetyl. A low-calorie bread spread has the non-absorbable, non-digestible polyol fatty acid polyester as its oil phase.

While perhaps not thought of as an emulsion by the lay person, cake batters can also be considered as fat-in-water emulsion systems; FOOD EMULSIONS, S. Friberg, ed., Marcel Dekker, Inc. New York 1976. Succinctly stated, a batter comprises a complex emulsion/-foam system which is processed by being heat set.

As is well known by bakers, badly prepared cakes suffer from a variety of practical problems, including slumping, low volume, dryness, poor crumb structure, too-rapid staling, and the like. Although the mode of handling and baking contributes to the overall quality of a baked cake, it is important not to underestimate the effect of the components of the cake batter, itself, to the overall quality of the finished product.

It has long been known that emulsifiers can be used in shortenings especially designed for cake baking (so-called "high-ratio shortenings") to overcome the aforementioned problems. High-ratio shortenings generally contain about 8% of various glyceride emulsifiers.

The alpha-hydroxy acid polyol ester emulsifiers of the present invention perform in a manner which is fully equivalent, or even superior, to the emulsifiers currently in use in cake mixes, cookie mixes, brownie mixes, and the like. Accordingly, the present invention also provides batter mixes for cakes, and the like, comprising the usual flour, shortening (e.g., edible, digestible triglyceride), sugar, etc., ingredients well-known to those skilled in the baking arts, together with the emulsifiers disclosed herein. In a low-calorie batter mix, the triglyceride shortening is replaced with the edible, non-absorbable, non-digestible, polyol polyesters herein.

Other compositions which fall within the scope of the present invention are those which, although not formulated as emulsions, interact with an external source of water to form an emulsion during use. For example, it is advantageous to provide cooking oils containing the emulsifiers herein so that the chef can use such products in the usual cooking mode, or can add water or vinegar to provide a salad dressing. Some products, such as peanut butter or candies, are not typically manufactured as emulsions. However, during mastication, such products mix with saliva, and the presence of the emulsifiers herein contributes importantly to ease-of-mastication and enhances the impression of product "smoothness". Other such products include emulsifiable "concentrates", to which water, milk, or the like, can be added by the user prior to ingestion.

Thus, in another of its embodiments, the present invention encompasses substantially water-free compositions in the form of emulsifiable mixtures, comprising:
(a) a fat or oil component; and
(b) from about 0.01% to about 10% by weight of the fat or oil component of the alpha-hydroxy acid polyol ester herein.

When such substantially water-free compositions are intended for ingestion, the selection of edible digestible and non-digestible fat and oil components is the same as that disclosed above for the water-containing compositions. The following are non-limiting examples of such compositions.

Typical, substantially water-free compositions include spreads in the form of peanut butter, or the like, comprising the emulsifiers herein and an oil component which comprises peanut oil, said composition additionally containing dispersed peanut particles. A low calorie version of this composition is also available by replacing the peanut oil with a liquid non-digestible polyol polyester.

Another substantially water-free composition is in the form of a confection, especially a chocolate candy, wherein the fat component comprises a confectioner's butter, e.g., natural or synthetic cocoa butter. A low calorie version is available by replacing all or part of the confectioner's butter with a solid, non-absorbable, non-digestible polyol polyester.

Other substantially water-free compositions comprise vegetable or non-vegetable (e.g., tallow; lard) cooking oils or shortenings and the emulsifiers herein.

Another substantially water-free composition comprises a non-absorbable, non-digestible polyol polyester and the emulsifier. Water or milk can be added to this product, in-use, to provide a low-calorie "milk-shake" type beverage.

A substantially water-free "concentrate" suitable for formulating a nutritious beverage by adding water or milk comprises the emulsifier, an oil phase, which is a digestible vegetable oil or a non-absorbable, non-digestible polyol polyester, and protein, especially soybean-derived protein.

The emulsion or emulsifiable mixture compositions of the present invention can be prepared in the same manner as when typical art-disclosed, non-hydroxylated emulsifiers are used. The alpha-hydroxy acid polyol ester emulsifiers herein can be simply blended or otherwise mixed into the compositions. Because the emulsions prepared with the present emulsifiers are less temperature sensitive than those prepared with the corresponding non-hydroxylated emulsifiers, emulsification of the compositions herein can be carried out over a broad temperature range, generally 5° C. to 95° C. Emulsification at room temperature is excellent.

Acceptable emulsions can be prepared using concentrations of the alpha-hydroxy acid polyol ester emulsifiers as low as 0.001% by weight of the fat or oil component in the composition. Typical use concentrations range from about 0.01% to about 10% by weight of the intended fat or oil content of the final composition. Preferably, the composition will contain from about 0.1% to about 1.0% by weight of the present emulsifier, based on the fat or oil content of the compositions.

Useful emulsions can be prepared when the weight ratio of the fat or oil component to the aqueous component is anywhere from about 1:200 to about 5:1. However, this ratio is preferably from about 1:20 to about 4:1, and more preferably from about 1:3 to about 3:1 for ease of preparation and stability of the emulsion.

As previously described, the alpha-hydroxy acid polyol esters of the present invention are also useful as detergent surfactants. While they are especially effective at removing greasy or oily soils from fabrics, they provide excellent overall cleaning under both cold and warm water laundering conditions.

The present alpha-hydroxy acid polyol ester surfactants may be employed by themselves, or in combination with detergent adjunct materials, as a separate laundry additive composition capable of boosting the cleaning of conventional detergent compositions. In this usage, the composition would simply be added to the laundering solution together with whatever fully-formulated detergent composition, bleach, etc., the user happens to choose. Alternatively, the composition can be used as a pretreatment composition to assist in the cleaning of difficult-to-remove soils and stains. More commonly, however, the alpha-hydroxy polyol esters herein are used as an essential component of a fully-formulated detergent composition.

Whatever the mode of usage, detergent compositions herein should contain a sufficient amount of the alphahydroxy acid polyol ester to provide a concentration in the laundering solution of from about 50 parts per million (ppm) to about 5000 ppm, preferably from about 100 ppm to about 500 ppm, and most preferably about 150 ppm to about 300 ppm. The weight percent of the alpha-hydroxy acid polyol ester used in a particular composition will depend somewhat on the type of product, its intended usage level, product density, and the like. Thus, the present surfactants can represent from about 0.005% to about 99%, preferably from about 3% to about 50%, more preferably from about 5% to about 25%, by weight of the detergent composition. Such detergent compositions may be in a solid form (e.g., granules, powders or laundry tablets), semi-solid pastes or gels, or they may be liquids. They may also be impregnated in or coated on a sheet substrate, or contained in a water-soluble packet.

Detergent compositions of the present invention preferably contain one or more organic cosurfactants selected from the group consisting of anionic, cationic, nonionic, ampholytic and zwitterionic surfactants, or mixtures thereof. These surfactants are described in U.S. Pat. No. 3,929,678, Laughlin, et al., issued Dec. 30, 1975, incorporated herein by reference. Useful cationic surfactants also include those described in U.S. Pat. No. 4,295,217, Murphy, issued Mar. 31, 1981 and in U.S. Pat. No. 4,222,905, Cockrell, issued Sept. 16, 1980, both incorporated herein by reference. The cosurfactant represents from about 1% to about 50%, preferably from about 2% to about 40%, more preferably from about 3% to about 20%, by weight of the detergent composition.

Anionic and zwitterionic surfactants are preferred cosurfactants herein because of their ability to boost the particulate soil removal performance of detergent compositions containing the present alpha-hydroxy acid polyol esters, while maintaining the excellent greasy/oily soil cleaning previously described.

Useful anionic surfactants specifically include those described in U.S. Pat. No. 3,929,678, cited above, from column 23, line 57 to column 35, line 20, and those described in U.S. Pat. No. 4,199,483, Jones, issued Apr. 22, 1980, from column 5, line 3 to column 6, line 26, incorporated herein by reference.

Specific preferred anionics for use herein include: the linear $C_9$–$C_{15}$ alkylbenzene sulfonates (LAS); the branched $C_9$–$C_{15}$ alkylbenzene sulfonates (ABS); the tallow alkyl sulfates, the coconut alkyl glyceryl ether sulfonates; the sulfated condensation products of mixed $C_{10}$–$C_{18}$ fatty alcohols with from about 1 to about 14 moles of ethylene oxide; and the mixtures of higher fatty acid soaps containing from 10 to 18 carbon atoms.

A preferred weight ratio of the alpha-hydroxy acid polyol ester herein to the anionic cosurfactant is from about 1:3 to about 3:1, more preferably from about 1:1 to about 2:1.

Useful zwitterionic surfactants herein specifically include those described in the above U.S. Pat. No. 3,929,678 from column 19, line 36, to column 23, line 56. However, the preferred zwitterionic cosurfactants herein are the ethoxylated zwitterionic compounds of the above patent and the biodegradable zwitterionic surfactants described in U.S. Pat. No. 4,301,044, Wentler et al., issued Nov. 17, 1981 incorporated herein by reference.

A preferred weight ratio of the alpha-hydroxy acid polyol ester herein to the zwitterionic surfactant is from about 1:1 to about 4:1, preferably from about 2:1 to about 3:1.

Other preferred cosurfactants include the amine oxides described in U.S. Pat. No. 4,276,205, Ferry, issued June 30, 1981, incorporated herein by reference, particularly column 3, lines 26–68.

The detergent compositions herein also preferably contain from about 1% to about 95%, more preferably from about 5% to about 75%, by weight of detergent builder materials. Detergency builders are generally characterized by an ability to sequester or precipitate water hardness ions, particularly calcium and magnesium. They may also be used to maintain or assist in maintaining an alkaline pH in a washing solution.

All manner of detergency builders commonly taught for use in detergent compositions are suitable for use herein. Useful builders include any of the conventional inorganic and organic water-soluble builder salts. Such detergency builders can be, for example, water-soluble salts of phosphates, pyrophosphates, orthophosphates, polyphosphates, phosphonates, carbonates, polyhydroxysulfonates, silicates, polyacetates, carboxylates, polycarboxylates and succinates.

Specific examples of inorganic phosphate builders include sodium and potassium tripolyphosphates, phosphates, and hexametaphosphates. The polyphosphonates specifically include, for example, the sodium and potassium salts of ethylene diphosphonic acid, the sodium and potassium salts of ethane 1-hydroxy-1,1-diphosphonic acid and the sodium and potassium salts of ethane-1,1,2-triphosphonic acid. Examples of these and other phosphorus builder compounds are disclosed in U.S. Pat. Nos. 3,195,513; 3,213,030; 3,422,021; 3,422,137; 3,400,176 and 3,400,148, incorporated herein by reference.

Non-phosphorus containing sequestrants can also be selected for use herein as the detergency builder. Specific examples of non-phosphorus, inorganic builder ingredients include water-soluble inorganic carbonate, bicarbonate, and silicate salts. The alkali metal, e.g., sodium and potassium, carbonates, bicarbonates, and silicates are particularly useful herein.

Water-soluble, non-phosphorus organic builders are also useful herein. For example, the alkali metal, ammonium and substituted ammonium polyacetates, carboxylates, polycarboxylates and polyhydroxysulfonates are useful builders in the present compositions. Specific examples of the polyacetate and polycarboxylate builder salts include sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid.

Highly preferred polycarboxylate builders herein are set forth in U.S. Pat. No. 3,308,067, Diehl, incorporated herein by reference. Examples of such materials include the water-soluble salts of homo and copolymers of aliphatic carboxylic acids such as maleic acid, itaconic acid, mesaconic acid, fumaric acid, aconitic acid, citraconic acid and methylenemalonic acid.

Additional, preferred builders herein include the water-soluble salts, especially the sodium and potassium salts, of carboxymethyloxymalonate, carboxymethyloxysuccinate, cis-cyclohexanehexacarboxylate, ciscyclopentanetetracarboxylate phloroglucinol trisulfonate, and the copolymer of maleic anhydride with vinyl methyl ether or ethylene.

Other suitable polycarboxylates for use herein are the polyacetal carboxylates described in U.S. Pat. No. 4,144,226, issued Mar. 13, 1979 to Crutchfield, et al., and U.S. Pat. No. 4,146,495, issued Mar. 27, 1979 to Crutchfield, et al., incorporated herein by reference. These polyacetal carboxylates can be prepared by bringing together under polymerization conditions an ester of glyoxylic acid and a polymerization initiator. The resulting polyacetal carboxylate ester is then attached to chemically stable end groups to stabilize the polyacetal carboxylate against rapid depolymerization in alkaline solution, converted to the corresponding salt, and added to a surfactant.

Another type of detergency builder material useful in the present compositions comprises a water-soluble material capable of forming a water-insoluble reaction product with water hardness cations in combination with a crystallization seed which is capable of providing growth sites for said reaction product. Such "seeded builder" compositions are disclosed in Belgian Pat. No. 798,856 issued Oct. 29, 1973, incorporated herein by reference. Specific examples of such seeded builder mixtures comprise: 3:1 wt. mixtures of sodium carbonate and calcium carbonate having 5 micron particle diameter; 2.7:1 wt. mixtures of sodium sequicarbonate and calcium carbonate having a particle diameter of 0.5 microns; 20:1 wt. mixtures of sodium sequicarbonate and calcium hydroxide having a particle diameter of 0.01 micron; and a 3:3:1 wt. mixture of sodium carbonate, sodium aluminate and calcium oxide having a particle diameter of 5 microns.

A further class of detergency builder materials useful in the present invention are the insoluble amorphous and crystalline aluminosilicates disclosed in the pending U.S. patent application of Rodriquez, et al., Ser. No. 049,704, filed June 18, 1979, incorporated herein by reference. Particularly useful aluminosilicates are those commonly known as Zeolites A, X and P(B).

Highly preferred non-phosphorus builder materials herein include sodium carbonate, sodium bicarbonate, sodium silicate, sodium citrate, sodium oxydisuccinate, sodium mellitate, sodium nitrilotriacetate, sodium ethylenediaminetetraacetate, and the sodium aluminosilicates, and mixtures thereof.

The detergent compositions herein preferably have an in-use pH in an aqueous laundry liquor of from about 9.0 to about 11.0, more preferably from about 9.4 to about 10.4. This pH is preferably provided by alkali metal silicate builder materials. The alkali metal silicates also enhance particulate soil removal from laundered fabrics when included in the detergent compositions of this invention. Moreover, the silicates provide corrosion inhibition protection to the metal parts of washing machines. Finally, the silicates provide a certain degree of crispness and pourability to spray-dried detergent granules which is very desirable to avoid lumping and caking, particularly during prolonged storage.

Suitable silicate solids have a molar ratio of $SiO_2$ to alkali metal oxide in the range from about 1:2 to about 4:1, preferably from about 1.6:1 to about 2.4:1. The sodium and potassium silicate solids are generally used, and the sodium silicates are most preferred.

The alkali metal silicates should represent from about 1% to about 15%, preferably from about 3% to about 8%, by weight of the detergent composition. The use of more than 10% by weight of the silicates in the spray-dried detergent compositions herein may present solubility problems in cold water usage conditions, especially when sodium aluminosilicate builders are also present in the detergent composition. U.S. Pat. No. 3,985,669, Krummel, et al., issued Oct. 12, 1976, incorporated herein by reference, discloses the preferred use of low levels of silicates in detergent compositions also containing aluminosilicate builders. However, admixing powdered alkali metal silicates with spray-dried granular compositions containing the aluminosilicates helps reduce interactions between the silicates and aluminosilicates and thus helps improve the solubility of granular detergents containing both components.

Granular detergent compositions herein preferably contain from about 20% to about 70% by weight of a detergent builder material selected from the group consisting of alkali metal phosphates, polyphosphates, carbonates, polyhydroxysulfonates, silicates, carboxylates, polycarboxylates, and aluminosilicates.

Liquid detergent compositions herein preferably contain the water-soluble detergency builders disclosed in U.S. Pat. No. 4,284,532, Leikhim et al., issued Aug. 18, 1981, from column 4, line 26 to column 6, line 26. More particularly, the organic builders for use in liquid compositions are the polycarboxylates, polyacetates, aminopolycarboxylates and phosphonates. Inorganic builders suitable for use in the liquid compositions herein are the polyphosphates, and preferably the water-soluble pyrophosphates.

Other optional components for use in liquid compositions herein include those described in the above Leikhim, et al., Patent, particularly from column 7, line 24 to column 9, line 66.

Other ingredients which are conventionally used in detergent compositions can be included in the detergent compositions of the present invention. These components include color speckles, bleaching agents and bleach activators, suds boosters or suds suppressors, anti-tarnish and anti-corrosion agents, soil suspending agents, soil release agents, dyes, fillers, optical brighteners, germicides, pH adjusting agents, non-builder alkalinity sources, hydrotropes, enzymes, enzyme-stabilizing agents, perfumes, and other optional detergent compounds.

An especially preferred optional component in the present detergent compositions is the alkylene oxide condensation product described in U.S. Pat. No. 4,276,205, Ferry, issued June 30, 1981, particularly from column 5, line 46 through column 6, line 52, incorporated herein by reference. Such alkylene oxide condensation products, which preferably are the polyethylene glycols, are believed to enhance the cold water cleaning of the present detergent compositions, especially on hard to remove particulate/oily combination soils or stains, such as those found on pillowcases.

The following non-limiting examples illustrate detergent compositions encompassed by the present invention.

All percentages, parts, and ratios used herein are by weight unless otherwise specified.

EXAMPLE I

| SALAD DRESSING | |
|---|---|
| Ingredient | Amount |
| Household Vinegar | 100 g. |

-continued

SALAD DRESSING

| Ingredient | Amount |
| --- | --- |
| Commercial Salad Oil | 182 g. |
| Table Salt | 6 g. |
| Alpha-hydroxy Monolaurin | to 0.125% of Salad Oil |

The foregoing composition was prepared by warming the alpha-hydroxy monolaurin in the salad oil with high speed blending (5 min.). The oil with blended alpha-hydroxy monolaurin emulsifier appeared clear, evidencing the good oil solubility of the emulsifier. The vinegar and salt were added, and the mixture was vigorously shaken to provide an excellent, emulsified salad dressing. In particular, the vinegar/oil separation time for the salad dressing was much longer (about 8 to 16 minutes, depending on the degree of separation measured) than separation times (25-40 seconds) of similar dressings prepared using a typical food emulsifier, glycerol monostearate.

In the composition of Example I, the alpha-hydroxy monolaurin is replaced by any of the following alpha-hydroxy acid polyol monoesters: the ethylene glycol, polyethylene glycol containing 2 or 5 ethylene oxide units, propylene glycol, polypropylene glycol containing 2 propylene oxide units, glycerol, polyglycerol containing 2 or 3 glycerol units, erythritol, xylitol, sorbitol, glucose, fructose, and sucrose monoesters of alpha-hydroxy acids derived from capric acid, myristic acid, palmitic acid, stearic acid, mixed coconut oil fatty acids, mixed plam oil fatty acids, mixed lard fatty acids, mixed soybean oil fatty acids, and mixed tallow fatty acids (preferred, for cost considerations), and mixtures thereof, respectively, and similar results are secured.

Comparable results are also obtained when the alpha-hydroxy monolaurin is replaced by the 1,2-di(alpha-hydroxy acid) and the 1-alpha-hydroxy acid esters of phosphatidyl choline and phosphatidyl ethanolamine, where the alpha-hydroxy acid is derived from capric acid, myristic acid, palmitic acid, stearic acid, mixed coconut oil fatty acids, mixed palm oil fatty acids, mixed lard fatty acids, mixed soybean oil fatty acids, and mixed tallow fatty acids (preferred, for cost considerations), and mixtures thereof, respectively.

Comparable emulsification is also obtained when, in the above compositions, the emulsifier represents about 0.05%, 0.1%, 0.2%, 0.6%, 1% or 3% by weight of the fat or oil component. Comparable results are also secured when the weight ratio of the oil component to the vinegar is about 3:1, 2:1, 1:1, 1:1.5 or 1:3.

EXAMPLE II

| ICING | |
| --- | --- |
| Ingredient | Amount |
| Fat* | 2 Kg |
| Milk Solids | 0.3 Kg |
| Water | 2 Kg |
| Powdered Sugar | 4 Kg |
| Salt | 0.05 Kg |
| Flavor | As Desired |
| Emulsifier** | 0.005 Kg |

*Commercial, hydrogenated vegetable oil shortening.
**Sucrose monoester of an alpha-hydroxy fatty acid prepared from mixed tallow fatty acids.

The foregoing icing composition is prepared by melting the emulsifier and blending it into the fat ingredient using a home-style, dual blade electric mixer. The other ingredients are added, and the mixture is blended for an additional 5-7 minutes. The resulting icing is stable, has an acceptable volume, and has a pleasant, smooth appearance which is especially desirable for icing and filling cakes, and the like.

In the icing composition of Example II, the emulsifier is replaced by a sucrose monoester of an alpha-hydroxy fatty acid derived from capric acid, lauric acid, myristic acid, palmitic acid, stearic acid, mixed palm oil fatty acids, mixed lard fatty acids, mixed soybean oil fatty acids, mixed peanut oil fatty acids, and mixtures thereof, respectively, and equivalent results are secured. Substantially similar results are obtained when the above sucrose monoesters are replaced with corresponding glucose, fructose, propylene glycol, glycerol, erythritol, xylitol, sorbitol, pentaerythritol, dipentaerythritol and inositol monoesters. Comparable results are also obtained when the above alpha-hydroxy acid monoesters are replaced by the correponding mono- and di-alpha-hydroxy acid esters of phosphatidyl choline and phosphatidyl ethanolamine.

EXAMPLE III

| LOW CALORIE SALAD DRESSING | |
| --- | --- |
| Ingredient | Amount |
| Sucrose Polyester* | 182 g. |
| Household Vinegar | 100 g. |
| Table Salt | 6 g. |
| Propylene Glycol Monoester of Alpha-hydroxy Lauric Acid | to 0.25% of Sucrose Polyester |

*Mixture of sucrose octaoleate with minor amounts of hepta- and hexa-oleate, prepared per U.S. Pat. No. 3,963,699.

The composition of Example III is prepared by warming the propylene glycol monoester in the sucrose polyester with high speed blending for about 5 minutes. The vinegar and salt are then added, and the mixture is vigorously shaken to provide an excellent, emulsified salad dressing.

EXAMPLE IV

| LOW CALORIE SALAD DRESSING - VITAMINIZED | |
| --- | --- |
| Ingredient | Amount |
| Sucrose Polyester* | 182 g. |
| Household Vinegar | 100 g. |
| Table Salt | 6 g. |
| Sorbitol Monoester of Alpha-hydroxy Lauric Acid | to 0.13% of Sucrose Polyester |
| Vitamin K | 10 RDA** |
| Irradiated Ergosterol (Vitamin D) | 10 RDA |
| Vitamin E | 10 RDA |
| Vitamin A | 10 RDA |

*Mixture of sucrose octaoleate with minor amounts of hepta- and hexa-oleate, prepared per U.S. Pat. No. 3,963,699.
**RDA represents the recommended daily allowance of the vitamin as specified by the United States Government. See U.S. Pat. Nos. 4,005,195 and 4,005,196.

The composition of Example IV is prepared by warming the sorbitol monoester in the sucrose polyester with high speed blending for about 5 minutes. The oil-soluble vitamins are then admixed with the sucrose polyester; the vinegar and salt are added, and the product is ready for use. During use, the product is vigorously shaken a few times to provide an excellent, emulsified, vitaminized low calorie salad dressing. Each serving (about 25-35 mls.) provides approximately 1 RDA of the listed fat-soluble vitamins.

In the compositions of Examples III and IV, the alpha-hydroxy acid polyol monoester is replaced by its corresponding derivative of capric acid, myristic acid, palmitic acid, stearic acid, mixed palm oil fatty acids, mixed lard fatty acids, mixed soybean oil fatty acids and mixed tallow fatty acids, and equivalent low calorie salad dressing emulsions are secured.

EXAMPLE V

| SALAD CREAM | |
|---|---|
| Ingredient | Amount |
| Commercial Salad Oil | 295 g. |
| Vinegar | 100 g. |
| Lemon Juice | 10 g. |
| Table Salt | 8 g. |
| Alpha-hydroxy Monomyristin | 2.1 g. |

The composition of Example V is prepared in the manner of the salad dressing of Example I to provide a rich, creamy salad dressing. In a low calorie mode, the commercial salad oil is replaced by 275 g. of sucrose octaoleate and 20 g. hardened palm oil (AAL agent).

EXAMPLE VI

Mayonnaise-Type Dressing

The compositions of Example V (both the regular and low-calorie versions are suitable) are whipped with a rotary mixer for about 3 minutes to provide a mayonnaise-type of dressing. In a preferred mode, an egg is added to the composition prior to mixing to enhance the richness of the whipped product.

EXAMPLE VII

| BEVERAGE CONCENTRATE | |
|---|---|
| Ingredient | Amount |
| Casein | 1.7 g. |
| Soy Protein | 1.6 g. |
| Commercial Salad Oil | 3.6 g. |
| Lactose | 4.7 g. |
| Sodium Chloride | 1.2 g. |
| Alpha-hydroxy Monolaurin | 0.25 g. |
| Vanilla | 0.005 g. |

The above emulsifiable beverage concentrate is prepared by blending the listed ingredients and packaging in a foil packet. In use, the packet of concentrate is admixed with 100 g. of water and shaken to provide a nutritious beverage in emulsion form.

A low-calorie version of the above beverage concentrate is prepared by replacing one-half of the salad oil with an equal amount of sucrose octaoleate. The triglyceride-derived calories in the product are thereby reduced by one-half.

EXAMPLE VIII

| PEANUT-BASED SPREAD | |
|---|---|
| Ingredient | Amount (%) |
| Peanuts | 93 |
| Peanut Oil | 6 |
| Salt (NaCl) | 0.75 |
| Diglycerol Monoester of Alpha-hydroxy Lauric Acid | 0.25 |

The whole, roasted peanuts are removed from their shells and ground in standard fashion. The diglycerol monoester is warmed in the peanut oil and added to the ground peanuts. The salt is added, and the composition is blended until substantially homogeneous. In a lower calorie version, the added peanut oil is replaced by an equivalent amount of sucrose octaoleate.

EXAMPLE IX

| CONFECTION | |
|---|---|
| Ingredient | Amount |
| Cocoa Butter | 20 g. |
| Cocoa Solids | 20 g. |
| Sugar | 47 g. |
| Peanuts (pieces) | 17 g. |
| Vanilla | 0.2 g. |
| Alpha-hydroxy Monopalmitin | 0.4 g. |

The above confection is prepared by melting the cocoa butter and alpha-hydroxy monopalmitin emulsifier together, and blending in the balance of the ingredients. The product is cooled before eating. When eaten, the emulsifier contributes importantly to the perceived "smoothness" of the confection.

EXAMPLE X

| MARGARINE | |
|---|---|
| Ingredient | Amount |
| Hydrogenated Palm Oil | 20 g. |
| Corn Oil | 50 g. |
| Milk | 65 g. |
| Salt | 0.5 g. |
| Emulsifier* | 0.2 g. |
| Diacetyl (butter flavor) | 0.002 g. |
| Artificial Color (carotene) | Optional |

*Sucrose monoester of the mixed alpha-hydroxy fatty acids derived from tallow.

The margarine is prepared by melting the hardened palm oil, corn oil and emulsifier, and blending in the balance of the ingredients. Upon cooling, the product is suitable for use as a bread spread, or the like, in the manner of margarine compositions. The emulsifier contributes importantly to the product's shelf-stability and excellent, non-waxy mouth-feel. In a low-calorie version, the corn oil is replaced by an equivalent amount of a non-absorbable, non-digestable polyol polyester (sucrose hexa-, hepta- and octa-oleates are preferred) and an excellent low calorie spread is secured. Such a composition additionally provides an antihypercholesterolemic benefit to the user.

EXAMPLE XI

| FROZEN DESSERT | |
|---|---|
| Ingredient | Amount |
| Sunflower Oil | 12 g. |
| Water | 24 g. |
| Milk Solids | 12 g. |
| Emulsifier* | 0.04 g |
| Butter Fat | 3.0 g. |
| Carrageenan | 1.2 g. |
| Corn Syrup (50% sugar) | 12 g. |
| Flavor | Optional |

*Triglycerol monoester of alpha-hydroxy stearic acid

The above dessert is prepared by melting the fat components with the emulsifier. The carrageenan is separately blended in the water. All ingredients are then combined and mixed until homogeneous. The product is refrigerated until semi-solid, at which point it is ready for use. A low calorie version of the product is prepared by replacing the sunflower oil with an equivalent amount of mixed sucrose octa-, hepta- and hexa-oleate esters.

EXAMPLE XII

BATTER

| Ingredient | Amount (Parts by Weight) |
|---|---|
| Cake Flour* | 100 |
| Shortening | 75 |
| Sugar | 130 |
| Egg | 95 |
| Milk | 70 |
| Baking Powder | 3 |
| Salt | 2.5 |
| Propylene Glycol Monoester of Alpha-hydroxy Lauric Acid** | to 1% of shortening |

*Chlorinated type.
**Pre-mixed into the shortening at 70° C.

The batter is prepared by making a paste of the fat (shortening with pre-mixed emulsifier) and flour, creaming in the sugar, then admixing the balance of the ingredients and whipping. The batter is then baked in standard fashion to provide a cake which is free from slump, exhibits good crumb texture and moistness, and has good volume. In a low calorie version, one-half the shortening is replaced by sucrose octapalmitate.

In the above batter composition, the propylene glycol monoester is replaced by the corresponding compounds derived from the following alpha-hydroxy fatty acids: alpha-hydroxy octanoic, alpha-hydroxy nonanoic, alpha-hydroxy decanoic, alpha-hydroxy undecanoic, alpha-hydroxy tridecanoic, alpha-hydroxy tetradecanoic, alpha-hydroxy pentadecanoic, alpha-hydroxy hexadecanoic, alpha-hydroxy heptodecanoic, alpha-hydroxy octadecanoic, alpha-hydroxy nonandecanoic, and alpha-hydroxy eicosanoic, respectively, and excellent batters are secured.

The foregoing are representative examples of fully-formulated emulsion compositions of the type provided by the present invention. The present invention also encompasses ingestible shortenings and cooking and salad oils, as well as low calorie versions of same comprising the non-absorbable, non-digestable polyol polyesters, containing the alpha-hydroxy acid polyol ester emulsifiers herein. Such compositions provide a convenient means whereby the user can formulate a wide variety of emulsion recipes while obtaining the advantages of the present emulsifiers. Representative examples of such compositions are as follows. In each instance, the compositions are prepared by simply warming the emulsifier in the fat or oil.

EXAMPLE XIII

SHORTENING

| Ingredient | Amount (%) |
|---|---|
| Hydrogenated Vegetable Oil | 99.4 |
| Alpha-hydroxy Monolaurin | 0.6 |

The above composition is especially suitable for preparing icings, cakes, cookies and brownies.

EXAMPLE XIV

LARD

| Ingredient | Amount (%) |
|---|---|
| Lard (winterized) | 99.2 |
| Sorbitol Monoester of Alpha-hydroxy Oleic Acid | 0.8 |

The composition of Example XIV is especially suitable for preparing pie crusts, pasta, and the like. Rendered tallow can be substituted for the lard.

EXAMPLE XV

SELF-CREAMING SALAD OIL

| Ingredient | Amount (%) |
|---|---|
| Safflower Oil (winterized) | 99.8 |
| Sucrose Monoester of Alpha-hydroxy Stearic Acid | 0.2 |

The composition of Example XV is especially useful for preparing salad dressings and sauces. Corn oil, sunflower seed oil and peanut oil can be substituted for the safflower oil.

EXAMPLE XVI

LOW CALORIE OIL

| Ingredient | Amount (%) |
|---|---|
| Sucrose Octaoleate | 98.5 |
| Ethylene Glycol Monoester of Alpha-hydroxy Lauric Acid | 1.5 |

The composition of Example XVI can be used in the manner of the composition of Example XV, when a low calorie recipe is desired.

EXAMPLE XVII

A skin moisturizing composition of the present invention is as follows:

| Ingredient | Amount (%) |
|---|---|
| Amerlate WFA* | 0.75 |
| Amerlate W** | 1.50 |
| Stearic Acid | 1.00 |
| Cetyl Alcohol | 2.75 |
| Alpha-hydroxy Monolaurin | 1.00 |
| 2-Pyrrolidinone | 8.00 |
| Carbopol 934*** | 3.25 |
| Propylene Glycol | 4.00 |
| Distilled Water | Balance to 100 |

*Mixture of lanolin fatty acids, commercially available from Amerchol Unit of CPC International
**Isopropyl ester of lanolin fatty acids, commercially available from Amerchol Unit of CPC International
***Polymer of acrylic acid cross-linked with polyalkyl ether of sucrose (M. Wt. 1,000,000), commercially available from B. F. Goodrich Chemical Co.

The above composition is a creamy liquid oil-in-water emulsion prepared by mixing the ingredients after heating to about 80° C. and then cooling to room temperature.

EXAMPLE XVIII

The cleaning performance of alpha-hydroxy monolaurin was tested under cold water laundering conditions. In the test, the alpha-hydroxy monolaurin was used in combination with a commercial detergent composition designed for use in warm water (40° C.), but the test was run using cold water (16° C.). The object of the test was to determine whether the alpha-hydroxy monolaurin could enhance the performance of the commercial product in cold water. Two types of soil were used in the test: simulated body soils (abbreviated "BBS" and "OHT" soils in Table 1) and natural facial soil collected on fabric swatches (Table 2). Test conditions were: 0.12% by weight of a commercial detergent composition in the laundering solution; 300 ppm alpha-hydroxy monolaurin as a detergent additive; 10 minute fabric wash in Tergotometer; and a water hardness of 7 grains/gallon (2 moles $Ca^{++}$; 1 mole $Mg^{++}$). The results were as follows.

TABLE 1

| Test Composition | Temperature | % Removal BBS | OHT |
|---|---|---|---|
| Commercial Detergent | 40° C. | 35(43)* | 25(32) |
| Commercial Detergent | 16° C. | 29(24) | 19(16) |
| Commercial Detergent + Alpha-Hydroxy Monolaurin | 16° C. | 42 | 39 |

*Values in parentheses from previous tests.

TABLE 2

| Test Composition | Temperature | Cleaning Performance* |
|---|---|---|
| Commercial Detergent | 40° C. | +1.34 (Avg. of 2 tests) |
| Commercial Detergent | 16° C. | −1.06 (Avg. of 2 tests) |
| Commercial Detergent + Alpha-hydroxy Monolaurin | 16° C. | +0.13 (Avg. of 2 tests) |

*As measured in "panel score units."

As can be seen from the foregoing, the alpha-hydroxy monolaurin substantially improved the cold water detergency performance of the commercial laundry detergent.

EXAMPLE XIX

A granular detergent composition according to the present invention is as follows.

| Ingredient | Percent (Wt.) |
|---|---|
| Sodium $C_{13}$ (avg.) Linear Alkylbenzene Sulfonate | 7.0 |
| Sodium Tripolyphosphate | 32.0 |
| Sodium Carbonate | 20.0 |
| Sodium Sulfate | 10.0 |
| Bentolite L Clay | 3.0 |
| Sodium Silicate (2.0 r.) | 6.0 |
| Alpha-hydroxy Monolaurin | 15.0 |
| Water and Miscellaneous | Balance to 100 |

*A calcium bentonite clay available from Georgia Kaolin Co.

The above composition is prepared by admixing all ingredients in a crutcher to form a homogeneous mix and then spray-drying the mixture using standard equipment.

The composition is added, at a level of about 1400 parts per million (ppm), to standard top-loading automatic washing machines containing water having a temperature of about 16° C. and a hardness of about 7 grains/gallon (2:1 $Ca^{++}:Mg^{++}$). A load of mixed fabrics is laundered in the resulting solution, which has a pH of about 9.7, using the machine manufacturer's instructions. The fabrics are then rinsed and dried.

The composition provides excellent overall cleaning of the fabrics. Excellent results are also obtained when the composition is used at a level of 1000 ppm or 2000 ppm in both cold and warm water.

Substantially similar cleaning results are obtained when the alpha-hydroxy monolaurin is replaced by any of the following alpha-hydroxy acid polyol monoesters: the ethylene glycol, polyethylene glycol containing 2 or 5 ethylene oxide units, propylene glycol, polypropylene glycol containing 2 propylene oxide units, glycerol, polyglycerol containing 2 or 3 glycerol units, erythritol, xylitol, sorbitol, glucose, fructose, and sucrose monoesters of alpha-hydroxy acids derived from capric acid, myristic acid, palmitic acid, stearic acid, mixed coconut oil fatty acids, mixed palm oil fatty acids, mixed lard fatty acids, mixed soybean oil fatty acids, and mixed tallow fatty acids (preferred, for cost considerations), and mixtures thereof, respectively, and equivalents results are secured.

Comparable results are also obtained when the alpha-hydroxy monolaurin is replaced by the 1,2-di(alpha-hydroxy acid) esters of phosphatidyl choline and phosphatidyl ethanolamine, where the alpha-hydroxy acid is derived from capric acid, myristic acid, palmitic acid, stearic acid, mixed coconut oil fatty acids, mixed palm oil fatty acids, mixed lard fatty acids, mixed soybean oil fatty acids, and mixed tallow fatty acids, and mixtures thereof, respectively.

EXAMPLE XX

Granular detergent compositions according to the present invention are as follows.

| Component | Percent (Wt.) A | B |
|---|---|---|
| Zwitterionic surfactant[1] | 10.0 | |
| 3-(N—coconutalkyl N,N—dimethyl ammonio)-2-hydroxy propane-1-sulfonate | | 8.0 |
| Alpha-hydroxy Monolaurin | 10.0 | |
| Propylene Glycol Monoester of Alpha-hydroxy Tallow Fatty Acid | | 12.0 |
| Sodium Tripolyphosphate | 18.0 | |
| Sodium Aluminosilicate (hydrated Zeolite A, particle Diameter 1–10 microns) | 18.0 | 12.0 |
| Sodium Nitrilotriacetate | | 32.0 |
| Sodium Carbonate | 12.0 | 10.0 |
| Sodium Silicate (2.0 r) | 3.0 | 2.0 |
| Sodium Sulfate | 20.0 | 14.0 |
| Water and miscellaneous | Balance to 100 | |

[1]$C_{18}H_{35}(CH_3)_2{}^+N—(CH_2CH_2O)_9CH_2CH_2SO_3{}^-$

The above compositions are prepared and used in the manner of Example XIX. The compositions also provide outstanding cleaning, both of particulate and oily soils, under cold or warm water laundering conditions.

EXAMPLE XXI

A liquid detergent composition according to the present invention is as follows.

| Ingredient | Percent (Wt.) |
|---|---|
| Dimethyl $C_{12-16}$ Alkyl Amine Oxide | 6.7 |
| Propylene Glycol Monoester of Alpha-hydroxy Lauric Acid | 11.5 |
| Potassium Toluene Sulfonate | 12.1 |
| Sodium Citrate | 10.0 |
| Monoethanolamine | 4.0 |
| Ethanol | 2.0 |
| Water and Miscellaneous | Balance to 100 |

The composition formed simply by mixing the components. It is suitable for use as a cold or warm water fabric laundering composition. The composition is especially useful when applied full strength to collars and cuffs of fabrics heavily stained with body soil. It is rubbed in briskly and the fabrics are laundered in standard fashion. The composition is also suitable for washing hard surfaces, including walls, woodwork, floors, metal surfaces, windows, and the like. For use as a laundry detergent, the composition is employed at a concentration range from about 1000 ppm to about 2000 ppm in the laundering liquor, depending on the fabric load and soil load. For use as a hard surface cleanser, concentrations in water of about 250 ppm are suitable for most cleaning purposes.

EXAMPLE XXII

A liquid detergent composition is as follows.

| Ingredient | Percent (Wt.) |
| --- | --- |
| Ditallow Dimethylammonium Chloride | 4.8 |
| $C_{12}$–$C_{13}$ $E_{6.5}$ Nonionic Surfactant* | 12.0 |
| Alpha-hydroxy Monolaurin | 12.0 |
| Ethanol | 14.8 |
| Sodium Citrate | 0.7 |
| Water and Miscellaneous | Balance to 100 |

*Condensation product of a $C_{12-13}$ linear primary alcohol with 6.5 moles (avg.) of ethylene oxide.

Usage of the above composition at a level of ½ cup provides outstanding cleaning of fabrics, particularly an oily soils, and additionally provides softening, static-control, and dye transfer inhibition benefits.

What is claimed is:

1. A polyol monoester or diester of an alpha-hydroxy carboxylic acid of the formula

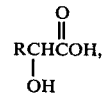

wherein R is a hydrocarbyl group containing from about 6 to about 20 carbon atoms and the polyol is the choline or ethanolamine ester of glycerol phosphoric acid having 0 or 1 of its hydroxyl groups esterified with a carboxylic acid containing from about 8 to about 22 carbon atoms.

2. A compound according to claim 1 wherein substituent R of the alpha-hydroxy carboxylic acid is an alkyl group containing from about 8 to about 18 carbon atoms.

3. A compound according to claim 2 wherein substituent R of the alpha-hydroxy carboxylic acid is an alkyl group containing from about 10 to about 16 carbon atoms.

4. A compound according to claim 1 or 3 which is a polyol diester of the alpha-hydroxy carboxylic acid.

* * * * *